United States Patent [19]

Ward

[11] Patent Number: 4,785,826
[45] Date of Patent: Nov. 22, 1988

[54] BIOPSY INSTRUMENT

[76] Inventor: John L. Ward, 1006 Barnwell St., Columbia, S.C. 29201

[21] Appl. No.: 20,858

[22] Filed: Mar. 2, 1987

[51] Int. Cl.⁴ ............................................. A61B 10/00
[52] U.S. Cl. .................................... 128/754; 128/310; 30/174; 30/278; 408/204; 408/207; 408/703
[58] Field of Search ............... 128/310, 305, 321, 322, 128/324, 749, 751, 754; 604/158, 264, 280; 30/174, 346.57, 353, 358, 366, 278, 279, 280; 408/204, 205, 207, 208, 209, 703

[56] References Cited

U.S. PATENT DOCUMENTS

| | | | |
|---|---|---|---|
| 2,496,111 | 1/1950 | Turkel | 128/2 |
| 2,850,007 | 5/1975 | Lingley | 128/2 |
| 2,869,541 | 1/1959 | Helmer et al. | 128/218 |
| 3,001,522 | 9/1961 | Silverman | 128/754 |
| 3,175,554 | 3/1965 | Stewart | 128/2 |
| 3,342,175 | 9/1967 | Bulloch | 128/2 |
| 3,598,108 | 8/1971 | Jamshidi | 128/2 B |
| 3,605,721 | 9/1971 | Hallac | 128/2 B |
| 3,628,524 | 12/1971 | Jamshidi | 128/2 B |
| 3,727,602 | 4/1973 | Hyden et al. | 128/2 B |
| 3,824,556 | 7/1974 | Berkovitz et al. | 128/419 P |
| 3,844,272 | 10/1974 | Banko | 128/2 B |
| 3,882,849 | 5/1975 | Jamshidi | 128/2 B |
| 3,893,445 | 7/1975 | Hofsess | 128/2 B |
| 4,010,737 | 3/1977 | Vilaghy et al. | 128/754 |
| 4,142,517 | 3/1979 | Stavropoulos et al. | 128/2 B |
| 4,266,555 | 5/1981 | Jamshidi | 127/753 |
| 4,356,828 | 11/1982 | Jamshidi | 128/754 |
| 4,378,810 | 4/1983 | Ishizaki et al. | 128/754 |
| 4,509,517 | 4/1985 | Zibelin | 128/321 |

FOREIGN PATENT DOCUMENTS 2177307 1/1987 United Kingdom ............... 128/754

*Primary Examiner*—Edward M. Coven
*Assistant Examiner*—Randy Citrin
*Attorney, Agent, or Firm*—Dority & Manning

[57] ABSTRACT

This invention relates to an instrument of a type known variously a a biopsy needle or cannula and used to gather tissue, and particularly soft tissue such as bone marrow, from living persons or animals for pathological study. The instrument retains a gathered tissue specimen by closing the end of a hollow member while the member is in the gathering position, and more particularly by deforming a flexible portion of the member. A pair of members are employed, one moving within the other. By a particular cooperation between the members, a flexible portion of the inner member is displaced or deformed to occlude an open, tissue receiving end thereof and thereby capture tissue and retain it against loss on removal of the instrument from the body of tissue into which it has been thrust.

8 Claims, 3 Drawing Sheets

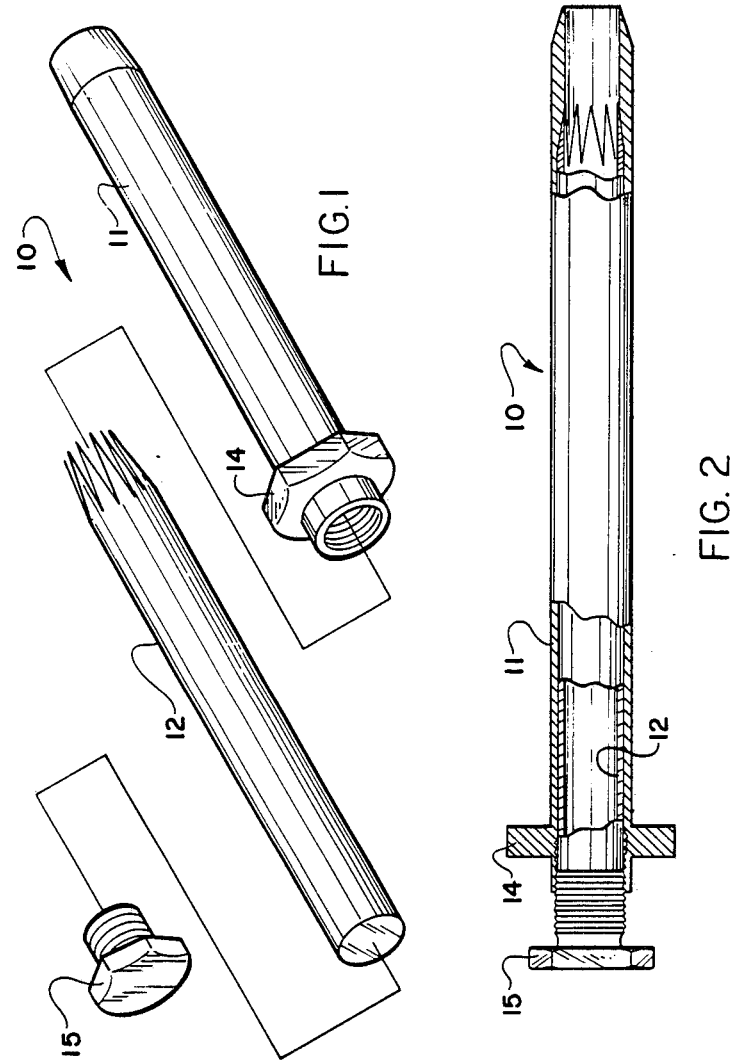

BIOPSY INSTRUMENT

FIELD AND BACKGROUND OF INVENTION

This invention relates to an instrument for gathering tissue for biopsy. More particularly, this invention relates to an instrument of a type known variously as a biopsy needle or cannula and used to gather tissue, and particularly soft tissue such as bone marrow, from living persons or animals for pathological study.

Such instruments are known generally and have been in wide use prior to the present invention. Examples may be found in the literature and from medical supply houses, and may include instruments such as are shown in Hallac U.S. Pat. No. 3,605,721; Lingley U.S. Pat. No. 2,850,007; and a series of United States Patents issued to Khosrow Jamshidi. In use, difficulties may be encountered with the loss of tissue specimens from within the instruments. More particularly, it is often difficult for a tissue specimen to be retained within an instrument during withdrawal of the instrument from the body of tissue into which it has penetrated, as the tissue is not fully separated from the living organism of which it forms a portion. Such loss of specimens is frustrating to the physician seeking to gather the tissue, and may subject a patient to needless imposition as repeated attempts are made to gather a specimen.

BRIEF DESCRIPTION OF INVENTION

With the foregoing in mind, it is an object of this invention to provide increased assurance that a tissue specimen gathered for biopsy is retained in the gathering instrument. In realizing this object of this invention, provision is made for occluding or closing the end of a hollow member within which the tissue is received while the member is in the gathering position with the body of tissue.

Yet a further object of this invention is to retain a gathered tissue specimen by closing the end of a hollow member while the member is in the gathering position, and more particularly by deforming a flexible portion of the member. In realizing this object of the invention, a pair of members are employed, one moving within the other. By a particular cooperation between the members, a flexible portion of the inner member is displaced or deformed to occlude an open, tissue receiving end thereof and thereby capture tissue and retain it against loss on removal of the instrument from the body of tissue into which it has been thrust.

BRIEF DESCRIPTION OF DRAWINGS

Some of the objects of the invention having been stated, other objects will appear as the description proceeds, when taken in connection with the accompanying drawings, in which:

FIG. 1 is an exploded perspective view of the members and elements of an instrument in accordance with this invention;

FIG. 2 is an elevation view, partly in section, of an assembled instrument in accordance with FIG. 1, showing the instrument as prepared for penetration into a body of tissue;

DETAILED DESCRIPTION OF INVENTION

While the present invention will be described more fully hereinafter with reference to the accompanying drawings, in which a preferred embodiment of the present invention is shown, it is to be understood at the outset of the description which follows that persons of skill in the appropriate arts may modify the invention here described while still achieving the favorable results of this invention. Accordingly, the description which follows is to be understood as being a broad, teaching disclosure directed to persons of skill in the appropriate arts, and not as limiting upon the present invention.

Figure 3:
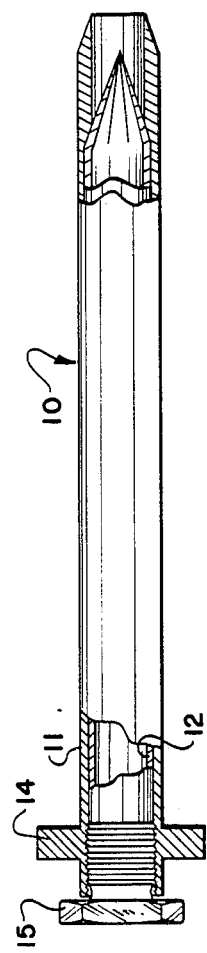
FIG. 3 is a view similar to FIG. 2, showing the instrument with the tissue receiving open end occluded for capturing a tissue specimen.

Referring now more particularly to FIG. 1, the instrument, generally indicated at 10, is shown to comprise first and second elongate, hollow, thin wall, right circular cylindrical members 11, 12. Each of the members has an open tissue penetrating end (to the right in each Figure) and a predetermined inside diameter. The second member has a predetermined outside diameter slightly less than the inside diameter of the first member for reception of the second member within the first member (FIGS. 2 and 3). The second member also has at least one segment thereof forming a flexible tissue capturing portion adjacent an end thereof proximate its open tissue penetrating end, of which more will be said later in this description.

In order to control axial movement of the members one relative to the other, for purposes described more fully hereinafter, the instrument has means coupling together the first and second members at ends thereof remote from the open tissue penetrating ends thereof. In the form shown in the drawings, that means takes the specific form of a pair of mating male and female threaded members 14, 15, one mounted on each of the first and second members 11, 12 for moving the members axially upon relative rotation therebetween. Persons skilled in the arts relating to medical instruments will be able to comprehend that other means may be provided to accomplish this function.

In order to capture a specimen of tissue received within the inner member 12, the present invention contemplates the provision of means on the first member and protruding into the hollow interior thereof proximate the open tissue penetrating end thereof for engaging the segment or segments forming the flexible tissue capturing portion of the second member upon axial movement of the members 11, 12 one relative to the other. On engaging the segments, and on continued axial movement, the means performs the function of deforming the segment or segments to occlude or close the open tissue penetrating end of the second member. By such occlusion or closing, the flexible tissue capturing portion of the second member, following penetration of the instrument into tissue from which a sample is to be taken for biopsy and reception of tissue within said second member, captures and retains a specimen of tissue.

The flexible tissue capturing portion may be formed by at least one flexible segment, and preferably is formed by a plurality of such segments. The segment(s) have a circumferential extent which converges toward said open tissue penetrating end of said second member, as shown most clearly in FIG. 2. Upon axial movement, the segment is, or segments are, deformed or bent inwardly toward the axis of the second member 12 (FIG. 3) to occlude or close the otherwise open end thereof. The second or inner member preferably is formed of a springy material to facilitate such deformation and the ultimate return of the member to its hollow, thin wall, right circular cylindrical shape for permitting expulsion of the tissue sample from the member. Where a plurality of segments are provided (as shown) a practical number of such segments is four, although a greater number have been shown in the drawings for clarity.

As described hereinabove, the segment(s) engage means on the first member and are deformed, bent or deflected thereby into the closing position. That means provided for thus deforming, bending or deflecting the segment(s) is shown (in FIGS. 2 and 3) as a shoulder means protruding into the interior of said first member. In that form of the invention, the first member 11 has a reduced inside diameter portion immediately adjacent the open tissue penetrating end thereof, and the means for engaging the segment(s) is a tapered shoulder surface defining a transition between the reduced inside diameter portion and the larger, predetermined, inside diameter which extends through the length of the member.

Figure 4:
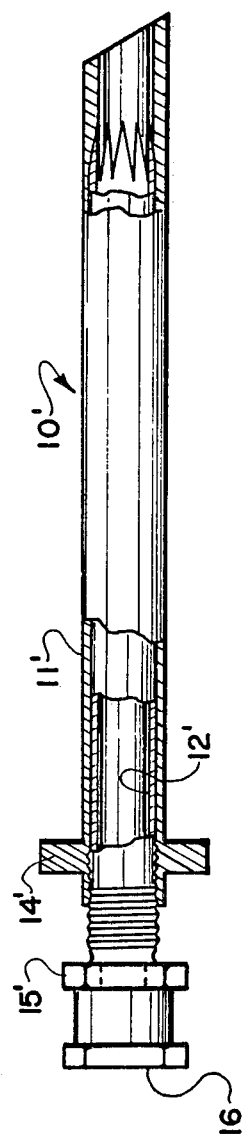
FIG. 4 is a view similar to FIG. 2 and showing a modified form of the instrument in accordance with this invention.

In order to facilitate penetration through bone or the like to reach soft tissue from which a biopsy sample is to be taken, the instrument of this invention may be modified and adapted to the use of an obturator such as is known from Lingley U.S. Pat. No. 2,850,007. As so modified, and as shown in FIG. 4 where primed notation has been used to identify compnents comparable to those described above, the threaded member 15' connected with the second member 12' is formed with an opening aligned with the hollow interior of the inner member. With such an opening provided, a obturator 16 may be inserted into the instrument in order to assure that undesired tissue is not captured within the instrument as penetration occurs and to facilitate penetration. Where such an obturator is used, it may be desirable to form the end of the instrument with a beveled edge, with the obturator 16 and the outer member 11' having such relative lengths that the slanted ends thereof are even and form a single surface. One further advantage of forming the threaded member 15' with an opening is the possibility of inserting a suitable member (possibly the obturator) for expelling a sample and assuring that the inner member is restored to the open position of FIGS. 1 and 2 after removal from the body of tissue and axial movement between the outer and inner members.

In use, the members 11, 12 are telescoped and the threaded members 14, 15 engaged by only a minimal amount to permit ease in handling of the instrument. The instrument (arranged as shown in FIG. 2) is then inserted into a body of tissue from which a sample is to be taken for biopsy. The threaded members are then turned one relative to the other to cause the elongated members 11, 12 to move axially one relative to the other and the inner member to close or occlude the tissue receiving opening of the inner member 12, thereby capturing or retaining within the instrument the tissue which has entered the bore of the instrument on insertion. The instrument may then be removed as indicated.

In the drawings and specifications there has been set forth a preferred embodiment of the invention and, although specific terms are used, the description thus given uses terminology in a generic and descriptive sense only and not for purposes of limitation.

What is claimed is:

1. An instrument for gathering tissue for biopsy, comprising:
   a first elongate, hollow, thin wall, right circular cylindrical member having an open tissue penetrating end and a predetermined inside diameter;
   a second elongate, hollow, thin wall, right circular cylindrical member having an open tissue penetrating end and a predetermined outside diameter slightly less than said inside diameter for reception of said second member within said first member, said second member having a flexible tissue capturing portion adjacent said open tissue penetrating end thereof;
   coupling means for coupling said first and second members at respective ends thereof opposite from said respective open tissue penetrating ends thereof and for controllably moving said members axially one relative to the other; and
   capturing means situated within said first member and proximate said open tissue penetrating end thereof, for engaging and inwardly deforming said flexible tissue capturing portion of said second member upon advancing axial movement of said second member relatively into said first member, so as to close said open tissue penetrating end of said second member; whereby
   said flexible tissue capturing portion of said second member, following penetration of the instrument into tissue from which a sample is to be taken for biopsy and reception of tissue within said hollow first and second members, may be closed for reliably capturing and retaining a specimen of tissue upon subsequent withdrawal of said instrument from the subject tissue.

2. An instrument according to claim 1, wherein:
   said capturing means includes shoulder means protruding into the interior of said first member.

3. An instrument according to claim 1 wherein:
   said first member has a reduced inside diameter portion immediately adjacent said open tissue penetrating end thereof; and
   further wherein said capturing means includes a tapered shoulder surface defining a transition between said reduced inside diameter portion and said predetermined inside diameter.

4. An instrument according to claim 1 wherein said flexible tissue capturing portion of said second member comprises at least one segment of said hollow, thin wall, right circular cylindrical second member, said segment having a circumferential extent which converges toward said open tissue penetrating end of said second member.

5. An instrument according to claim 1 wherein said flexible tissue capturing portion of said second member comprises a plurality of segments of said hollow, thin wall, right circular cylindrical second member, said segments each having a circumferential extent which converges toward said open tissue penetrating end of said second member.

6. An instrument according to claim 1 wherein said flexible tissue capturing portion of said second member comprises four segments of said hollow, thin wall, right circular cylindrical second member, said segments each having a circumferential extent which converges toward said open tissue penetrating end of said second member.

7. An instrument for gathering tissue for biopsy and comprising a first elongate, hollow, thin wall, right circular cylindrical member having an open tissue penetrating end and a predetermined inside diameter; a second elongate, hollow, thin wall, right circular cylindrical member having an open tissue penetrating end and a predetermined outside diameter slightly less than said inside diameter for reception of said second member within said first member, said second member having at least one segment thereof forming a flexible tissue capturing portion adjacent said open tissue penetrating end thereof; coupling means for coupling said first and second members at respective ends thereof remote from said open tissue penetrating ends thereof and for controllably moving said members axially one relative to the other; and capturing means, within said first member and protruding axially inward into the hollow interior thereof proximate said open tissue penetrating and thereof, for engaging said segment forming said flexible tissue capturing portion of said second member and inwardly deforming same upon advancing axial movement of said second member relatively into said first member, for deforming said segment to occlude said open tissue penetrating end of said second member; whereby said flexible tissue capturing portion of said second member, following penetration of the instrument into tissue from which a sample is to be taken for biopsy and reception of tissue within said first and second members, may be closed for capturing and retaining a specimen of tissue upon such subsequent withdrawal of said instrument from the subject tissue.

8. An instrument according to claim 7 wherein said coupling means includes a pair of mating male and female threaded members, one mounted on each of said first and second members for moving said member axially upon relative rotation therebetween

* * * * *